United States Patent
Schwede et al.

(10) Patent No.: US 7,148,213 B2
(45) Date of Patent: *Dec. 12, 2006

(54) ANTIGESTAGENICALLY ACTIVE STEROIDS WITH A FLUORINATED 17α-ALKYL CHAIN

(75) Inventors: Wolfgang Schwede, Berlin (DE); Arwed Cleve, Berlin (DE); Ulrich Klar, Berlin (DE); Gunter Neef, Berlin (DE); Kristof Chwalisz, Arzt (DE); Martin Schneider, Berlin (DE); Ulrike Fuhrmann, Berlin (DE); Holger Heb-Stumpp, Berlin (DE)

(73) Assignee: Schering AG, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 10/948,652

(22) Filed: Sep. 24, 2004

(65) Prior Publication Data

US 2005/0080060 A1  Apr. 14, 2005

Related U.S. Application Data

(63) Continuation of application No. 10/304,742, filed on Nov. 27, 2002, now Pat. No. 6,806,263, which is a continuation of application No. 09/978,689, filed on Oct. 18, 2001, now Pat. No. 6,503,895, and a continuation of application No. 09/516,359, filed on Mar. 1, 2000, now Pat. No. 6,316,432, and a continuation of application No. 09/020,947, filed on Feb. 9, 1998, now abandoned.

(30) Foreign Application Priority Data

Feb. 7, 1997 (DE) ................................ 197 06 061

(51) Int. Cl.
*A61K 31/56* (2006.01)
(52) U.S. Cl. .................. 514/179; 514/181; 514/182
(58) Field of Classification Search ................ 514/179, 514/181, 182
See application file for complete search history.

(56) References Cited

U.S. PATENT DOCUMENTS 4,912,097 A  3/1990  Teutsch et al.
5,006,518 A  4/1991  Moguilewsky et al.
5,064,822 A  11/1991  Philibert et al.
5,132,299 A  7/1992  Ottow et al.
5,272,140 A  12/1993  Loozen
5,843,933 A  12/1998  Cleve et al.
6,316,432 B1  11/2001  Schwede et al.
6,503,895 B1  1/2003  Schwede et al.

FOREIGN PATENT DOCUMENTS

| DE | 3844408 | 7/1989 |
|---|---|---|
| EP | 245 170 | 11/1987 |
| EP | 0310541 | 9/1988 |
| EP | 299 913 | 1/1989 |
| EP | 369 881 | 5/1990 |

OTHER PUBLICATIONS

Bianchi, "1-Pharmacology," *Chemical Abstracts*, vol. 123, No. 21 (1995).
Wang et al., "Trifluoromethylation of steroidal ketones," *Journal of Fluorine Chemistry*, 69, pp. 1-3 (1994).

*Primary Examiner*—Barbara P. Badio
(74) *Attorney, Agent, or Firm*—Millen, White, Zelano &Branigan P.C.

(57) ABSTRACT

This invention describes the new 17α-fluoroalkyl steroids of general formula I

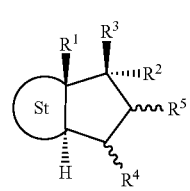

as well as their physiologically compatible salts with bases.

The new compounds have an extraordinary strong antigestagenic action and are suitable for the production of pharmaceutical preparations.

27 Claims, No Drawings

ANTIGESTAGENICALLY ACTIVE STEROIDS WITH A FLUORINATED 17α-ALKYL CHAIN

This application is a continuation of application Ser. No. 10/304,742 filed Nov. 27, 2002, now U.S. Pat. No. 6,806,263, which is a continuation of Ser. No. 09/978,689, filed Oct. 18, 2001, now Pat. No. 6,503,895 and a continuation of application Ser. No. 09/516,359, filed Mar. 1, 2000, now U.S. Pat. No. 6,316,432 and a continuation of application Ser. No. 09/020,947, filed Feb. 9, 1998, now abandoned.

This invention relates to antigestagenically active steroids with a fluorinated 17α-alkyl chain, process for their production, pharmaceutical preparations that contain the latter and their use for the production of pharmaceutical agents.

The invention relates to 17α-fluoroalkyl steroids of general formula I

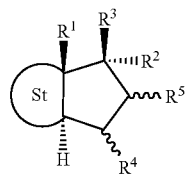

I in which
$R^1$ stands for a methyl or ethyl group,
$R^2$ stands for a radical of formula $C_nF_mH_o$, whereby n is 2, 3, 4, 5 or 6, m>1 and m+o=2n+1,
$R^3$ stands for a free, etherified or esterified hydroxy group,
$R^4$ and $R^5$ each stand for a hydrogen atom, or together for an additional bond or a methylene group,
St stands for a steroidal ABC-ring system of partial formula A, B or C

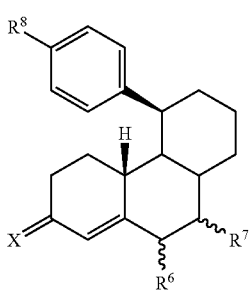

A

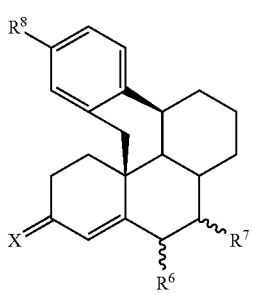

B

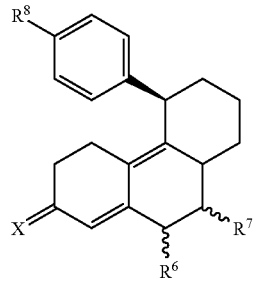

C in which
$R^6$ means a hydrogen atom, a straight-chain $C_1$–$C_4$ alkyl group or branched $C_3$–$C_4$ alkyl group or a halogen atom,
$R^7$ means a hydrogen atom, a straight-chain $C_1$–$C_4$ alkyl group or a branched $C_3$–$C_4$ alkyl group, or
if St stands for a steroidal ABC-ring system A or B, in addition
$R^6$ and $R^7$ together can mean an additional bond,
X means an oxygen atom, a hydroxyimino grouping =N—OH or two hydrogen atoms,
$R^8$ means a radical Y or an aryl radical that is optionally substituted with Y, whereby Y is a hydrogen atom, a halogen atom, an —OH, —$NO_2$, —$N_3$, —CN, —$NR^{9a}R^{9b}$, —$NHSO_2R^9$, —$CO_2R^9$, $C_1$–$C_{10}$ alkyl, $C_1$–$C_{10}$ alkoxy, $C_1$–$C_{10}$ alkanoyloxy, benzoyloxy, $C_1$–$C_{10}$ alkanoyl, $C_1$–$C_{10}$ hydroxyalkyl or benzoyl group, and $R^{9a}$ and $R^{9b}$ are the same or different and represent a hydrogen atom or a $C_1$–$C_{10}$ alkyl group, $R^9$ is a hydrogen atom or $C_1$–$C_{10}$ alkyl,
and for —$NR^{9a}R^{9b}$ radicals, as well as their physiologically compatible salts with acids and for —$CO_2R^9$ radicals with $R^9$ meaning hydrogen, as well as their physiologically compatible salts with bases.

The wavy lines mean that the substituent in question can be in α- or β-position.

In the alkyl groups that are mentioned within the scope of this invention, these are the methyl, ethyl, n- or iso-propyl, n-, iso- or tert-butyl groups, for example.

The other $C_1$–$C_{10}$ alkyl groups, Y, $R^9$, $R^{9a}$, $R^{9b}$, have the higher homologues in addition, such as, for example, the pentyl, neo-pentyl, hexyl to decyl groups, for example.

$C_1$–$C_{10}$ alkyl groups are to be understood to encompass, however, carbocyclic or alkylcycloalkyl groups as well with up to 10 carbon atoms, for example the cyclopropyl, cyclopentyl, cycloheptyl, methylcyclopropyl, methylcyclopentyl or methylcyclohexyl radical. A methyl or ethyl group is preferred for all cases above.

$C_1$–$C_{10}$ alkoxy, groups are the radicals that are lengthened by one oxygen atom and derived from the alkyl groups that are mentioned above, thus, e.g., the methoxy, ethoxy, n- or iso-propoxy, n-, iso- or tert-butoxy radical.

$C_1$–$C_{10}$ alkanoyl is defined as the acyl radicals of straight-chain and branched $C_1$–$C_{10}$ alkanecarboxylic acids, thus, for example, the formyl, acetyl, propionyl, butyryl or iso-butyryl radical, etc.

$C_1$–$C_{10}$ Alkanoyloxy radicals are the radicals of the above alkanoyl radicals that are lengthened by one oxygen atom, thus, e.g., the acetyloxy, propionyloxy, and butyryloxy radical.

If a halogen atom is mentioned as a substituent, this can be a fluorine, chlorine or bromine atom. Fluorine is preferred.

For radicals $R^2$, perfluorinated side chains of length n=2–4 are to be preferred and among the latter, in turn the pentafluoroethyl unit is especially to be preferred.

$R^3$ stands primarily for a free hydroxy group.

In the case of an etherified or esterified hydroxy group as a 17β-substituent, the latter is preferably etherified with a $C_1$–$C_{10}$ alkyl group or esterified with a $C_1$–$C_{10}$ alkanoyl group. For this alkyl or alkanoyl group, the same meanings as above hold true. The etherification or esterification of the hydroxy group is carried out according to the methods that are familiar to one skilled in the art.

$R^4$ and $R^5$ preferably each stand for hydrogen atoms or together for an additional bond.

If $R^8$ is a group Y, this is preferably a $C_1$–$C_{10}$ alkanoyl or (1-hydroxy)-$C_1$–$C_{10}$ alkyl group, whereby among these radicals, the acetyl and the propionyl group are especially to be preferred.

Preferred carbocyclic or heterocyclic aryl radicals are phenyl, 1- or 2-naphthalinyl, 0.2- or 3-furanyl, 2- or 3-benzofuranyl, 2- or 3-thienyl, 2-, 3- or 4-pyridinyl. As substituted aryl radical $R^8$ (e.g., substituted one or up to several (e.g., 2–3) times with Y), primarily 4-cyanophenyl and a 4-halophenyl radical, especially the 4-fluorophenyl radical, can be cited.

Among all the radicals that are mentioned as preferred for $R^8$, $R^8$ in the meaning of Y and Y in turn equal to acetyl is especially to be preferred.

The compounds that are mentioned below are especially preferred according to the invention:

11β-(4-Acetylphenyl)-17β-hydroxy-17α-(1,1,2,2,2-pentafluoroethyl)estr-4-en-3-one;

4'-[17β-hydroxy-3-oxo-17α-(1,1,2,2,2-pentafluoroethyl) estr-4-en-11β-yl][1,1'-biphenyl]-4-carbonitrile;

11β-(4'-fluoro-[1,1'-biphenyl]-4-yl)-17β-hydroxy-17α-(1,1,2,2,2-pentafluoroethyl)estr-4-en-3-one;

17β-hydroxy-17α-(1,1,2,2,2-pentafluoroethyl)-11β-[4-(3-pyridinyl)phenyl]estr-4-en-3-one;

11β-(4-acetylphenyl)-17β-hydroxy-17α-(1,1,2,2,2-pentafluoroethyl)estra-4,15-dien-3-one;

4'-[17β-hydroxy-3-oxo-17α-(1,1,2,2,2-pentafluoroethyl) estra-4,15-dien-11β-yl][1,1'-biphenyl]-4-carbonitrile;

11β-(4'-fluoro[1,1'-biphenyl]-4-yl)-17β-hydroxy-17α-(1,1,2,2,2-pentafluoroethyl)estra-4,15-dien-3-one;

17β-hydroxy-17α-(1,1,2,2,2-pentafluoroethyl)-11β-[4-(3-pyridinyl)phenyl]estra-4,15-dien-3-one;

11β-(4-acetylphenyl)-17β-hydroxy-17α-(1,1,2,2,2-pentafluoroethyl)estra-4,9-dien-3-one;

4'-[17β-hydroxy-3-oxo-17α-(1,1,2,2,2-pentafluoroethyl) estra-4,9-dien-11β-yl][1,1'-biphenyl]-4-carbonitrile;

11β-(4'-fluoro[1,1'-biphenyl]-4-yl)-17β-hydroxy-17α-(1,1,2,2,2-pentafluoroethyl)estra-4,9-dien-3-one;

17β-hydroxy-17α-(1,1,2,2,2-pentafluoroethyl)-11β-[4-(3-pyridinyl)phenyl]estra-4,9-dien-3-one;

11β-(4-acetylphenyl)-17β-hydroxy-17α-(1,1,2,2,2-pentafluoroethyl)estra-4,9,15-trien-3-one;

4'-[17β-hydroxy-3-oxo-17α-(1,1,2,2,2-pentafluoroethyl) estra-4,9,15-trien-11β-yl][1,1'-biphenyl]-4-carbonitrile;

11β-(4'-fluoro[1,1'-biphenyl]-4-yl)-17β-hydroxy-17α-(1,1,2,2,2-pentafluoroethyl))estra-4,9,15-trien-3-one;

17β-hydroxy-17α-(1,1,2,2,2-pentafluoroethyl)-11β-[4-(3-pyridinyl)phenyl]estra-4,9,15-trien-3-one;

6'-acetyl-9,11α-dihydro-17β-hydroxy-17α-(1,1,2,2,2-pentafluoroethyl)-4'H-naphth[3',2',1':10,9,11]estr-4-en-3-one;

4-[9,11α-dihydro-17β-hydroxy-3-oxo-17α-(1,1,2,2,2-pentafluoroethyl)-4'H-naphth[3',2',1':10,9,11]estr-4-en-6'-yl]benzonitrile;

9,11α-dihydro-6'-(4-fluorophenyl)-17β-hydroxy-17α-(1,1,2,2,2-pentafluoroethyl)-4'H-naphth[3',2',1':10,9,11]estr-4-en-3-one;

9,11α-dihydro-17β-hydroxy-17α-(1,1,2,2,2-pentafluoroethyl)-6'-(3-pyridinyl)-4'H-naphth[3',2',1':10,9,11]estr-4-en-3-one;

6'-acetyl-9,11α-dihydro-17β-hydroxy-17α-(1,1,2,2,2-pentafluoroethyl)-4'H-naphth[3',2',1':10,9,11]estra-4,15-dien-3-one;

4-[9,11α-dihydro-17β-hydroxy-3-oxo-17α-(1,1,2,2,2-pentafluoroethyl)-4'H-naphth[3',2',1':10,9,11]estra-4,15-dien-6'-yl]be 9,11α-dihydro-6'-(4-fluorophenyl)-17β-hydroxy-17α-(1,1,2,2,2-pentafluoroethyl)-4'H-naphth[3',2',1':10,9,11]estra-4,15-dien-3-one;

9,11α-dihydro-17β-hydroxy-17α-(1,1,2,2,2-pentafluoroethyl)-6'-(3-pyridinyl)-4'H-naphth[3',2',1':10,9,11]estra-4,15-dien-3-one;

17β-hydroxy-11β-(4-hydroxyphenyl)-17α-(1,1,2,2,2-pentafluoroethyl)estra-4,9-dien-3-one;

17β-hydroxy-11β-(4-hydroxyphenyl)-17α-(1,1,2,2,2-pentafluoroethyl)estr-4-en-3-one;

9,11α-dihydro-6',17β-dihydroxy-17α-(1,1,2,2,2-pentafluoroethyl)-4'H-naphth[3',2',1':10,9,11]estr-4-en-3-one;

11β-[4-(acetyloxy)phenyl]-17β-hydroxy-17α-(1,1,2,2,2-pentafluoroethyl)estra-4,9-dien-3-one;

11β-[4-(acetyloxy)phenyl]-17β-hydroxy-17α-1,1,2,2,2-pentafluoroethyl)estr-4-en-3-one 6'-(acetyloxy)-9,11α-dihydro-17β-hydroxy-17α-(1,1,2,2,2-pentafluoroethyl)-4'H-naphth[3',2',1':10,9,11]estr-4-en-3-one;

17β-hydroxy-11β-[4-(hydroxymethyl)phenyl]-17α-(1,1,2,2,2-pentafluoroethyl)estra-4,9-dien-3-one;

17β-hydroxy-11β-[4-(hydroxymethyl)phenyl]-17α-(1,1,2,2,2-pentafluoroethyl)estr-4-en-3-one;

9,11α-dihydro-17β-hydroxy-6'-(hydroxymethyl)-17α-(1,1,2,2,2-pentafluoroethyl)-4'H-naphth[3',2',1':10,9,11]estr-4-en-3-one;

4-[17β-hydroxy-3-oxo-17α-(1,1,2,2,2-pentafluoroethyl) estra-4,9-dien-11β-yl]benzaldehyde;

4-[17β-hydroxy-3-oxo-17α-(1,1,2,2,2-pentafluoroethyl) estr-4-en-11β-yl]benzaldehyde;

9,11α-dihydro-17β-hydroxy-3-oxo-17α-(1,1,2,2,2-pentafluoroethyl)-4'H-naphth[3',2',1':10,9,11]estr-4-en-6'-al;

4-[17β-hydroxy-3-oxo-17α-(1,1,2,2,2-pentafluoroethyl) estra-4,9-dien-11β-yl]benzoic acid methyl ester;

4-[17β-hydroxy-3-oxo-17α-(1,1,2,2,2-pentafluoroethyl) estr-4-en-11β-yl]benzoic acid methyl ester;

9,11α-dihydro-17β-hydroxy-3-oxo-17α-(1,1,2,2,2-pentafluoroethyl)-4'H-naphth[3',2',1':10,9,11]estr-4-en-6'-carboxylic acid methyl ester;

17β-hydroxy-11β-[4-(1-hydroxyethyl)phenyl]-17α-(1,1,2,2,2-pentafluoroethyl)estra-4,9-dien-3-one;

17β-hydroxy-11β-[4-(1-hydroxyethyl)phenyl]-17α-(1,1,2,2,2-pentafluoroethyl)estra-4,9-diene-3-one;

9,11α-dihydro-17β-hydroxy-6'-(1-hydroxyethyl)-17α-(1,1,2,2,2-pentafluoroethyl)-4'H-naphth[3',2',1':10,9,11]estr-4-en-3-one.

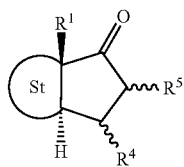

The establishment of fluorinated side chains in the 17α-position is carried out analogously to processes that have been described in many cases for other side chains by nucleophilic addition of an organometallic compound of formula $MC_nF_mH_o$ to a 17-ketone of general formula II, whereby M stands for a metal in the meaning of, e.g., Li, Na, K, Mg-halogen (halogen=Cl, Br, I) or other metals, and n, m and o have the meaning that is already indicated in general formula I. To be preferred is the addition of Grignard reagents ($C_nF_mH_o$Mg-halogen) or the lithium-organic compounds such as $LiC_nF_mH_o$. For the introduction of perfluorinated side chains, the generation of lithium-organic reagents starting from the corresponding iodides by means of a methyllithium/lithium bromide complex (J. Org. Chem. 1987, 52, 2481 and Tetrahedron Lett. 1985, 26, 5243) is especially suitable.

Substituents $R^1$, $R^4$, $R^5$ and St that are mentioned in general formula II have the meanings that are already indicated in general formula I, whereby functional groups that are present in St optionally can be protected according to processes known to one skilled in the art. Especially carbonyl groups, such as, e.g., the 3-keto groupings, are protected in most cases in a suitable way, e.g., by the formation of a corresponding ketal or reduction to a hydroxy group and optionally conversion of this hydroxy group into an ether or ester.

As a ketal protective group, for example, the ethylenedioxy or the 2,2-dimethlpropylene-1,3-dioxy group can be mentioned. Other standard keto protective groups are also considered. In the case of a protected hydroxy group, the latter can be protected, for example, in the form of methoxymethyl, methoxyethyl, tetrahydroxypyranyl or silyl ether. By cleavage of the protective group and oxidation of the free hydroxy group, the keto group is obtained.

In a suitable stage after the 17α-side chain has been added, the protective groups are then removed in a known way and optionally a hydroxy group is oxidized to the corresponding keto group.

The addition of the 17α-side chain can also be carried out in a selective manner, however, in the presence of other free carbonyl groups, e.g., also the 3-keto group.

The starting materials of general formula II that are used for the production of the compounds of general formula I are described in a whole series of patents, patent applications and publications:

EP-A 0 057 115, EP-A 0 129 499, EP-A 0 259 2489, EP-A 0 186 834, EP-A 0 447 014; EP-A-0 116 974, EP-A 0 190 759, EP-A 0 147 361, EP-A 192 598, EP-A 0 283 428, EP-A 0 404 283, WO-A 89/00578, WO-A 91/18917, WO-A 91/18918, WO-A 92/11277, WO-A 92/11278, WO-A 93/23020, Steroids 44 (1984), 349 as well as other relevant bibliographic references that are known to one skilled in the art who is active in this field.

In the above-mentioned industrial-property rights, the introduction of radicals $R^4$, $R^5$, $R^6$, $R^7$ and $R^8$, which occur there analogously to the radicals that are to be claimed here, is also described.

In general, the addition of the side chain with a free 17-keto group can be done at any intermediate stage in synthesis.

If the introduction of the fluorinated 17α-alkyl side chain is carried out in an early synthesis intermediate stage, the establishment of additional radicals $R^6$, $R^7$ and $R^8$ that are mentioned in St can be performed in the presence of this 17α-side chain according to known processes, as they were described in, i.a., the above-mentioned patents, patent applications and publications.

The new compounds of general formula I are valuable pharmaceutical active ingredients. They are distinguished by a very strong antigestagenic activity. These are competitive progesterone antagonists, since they displace the progesterone from its receptor. At the same time, other endocrine side effects, such as, e.g., androgenic, estrogenic or antiglucocorticoidal activity are present if at all, only to a small extent. The compounds can therefore be used for medicinal purposes.

Compounds with antigestagenic activity (competitive progesterone antagonists) became known for the first time in 1982 (RU 486=EP-A 0 057 115) and have since been described extensively in, i.a., the already mentioned patent and bibliographic citations found.

Among the previously disclosed compounds, there are none with a multiply fluorinated 17α-alkyl side chain that contains at least 2 carbon atoms. Only in WO83/03099 is it stated that the 3-keto-$\Delta^{4,9}$-19-nor steroids disclosed there can carry a 17α-alkyl side chain, which optionally can be substituted with a halogen atom. Fluorine is not mentioned as a halogen. Concrete examples with a 17α-alkyl chain that has at least 2 carbons previously did not exist at all.

Active ingredients of this type with strong antigestagenic activity are suitable for inducing abortions, since they displace from the receptor the progesterone that is necessary to maintain the pregnancy. They are therefore valuable and advantageous with respect to their use for postcoital birth control.

The compounds of general formula I according to the invention are also suitable for the production of preparations for female contraception (WO-A 93/23020, WO-A 93/21927).

In addition, they can be used to counteract hormonal irregularities, for triggering menstruation and for inducing labor. Other types of indications in the field of gynecology are the hormone replacement therapy (WO-A 94/18983), treatment of symptoms that accompany dysmenorrhea and endometriosis (EP-A 0 266 303) as well as myomas.

The compounds according to the invention exert strong antitumor activity in progesterone receptor positive rodent and human breat cancer models. Antiproliferative activity was observed in vitro in the human T47D breast cancer cell line. In vivo tumor inhibiting effects have been proven in the MXT-mammary carcinoma of the mouse and in the chemically induced mammary carcinoma models of the rat (NMU: N-nitroso methyl urea; DMBA: dimethylbenzanthracene.

The compounds according to the invention are thus highly suitable for the treatment of hormone-dependent carcinomas, for example, for treatment of the progesterone receptor positive mammary carcinoma. The compounds according to the invention can be used in the therapy of hormone dependent carcinomas for the first line therapy as well as for second line therapy, especially after tamoxifen failure.

The antigestagenically active compounds of general formula I according to the invention can also be used in combination with antiestrogenically active compounds for the production of pharmaceutical preparations for the treatment of hormone-dependent tumors (EP-A 0 310 542), for inducing labor, for termination of pregnancy and for treatment of gynecological disorders (EP-A 0 310 541) and for female contraception (WO 96/19997). In the treatment of hormone dependent carcinoma, the antigestagen and the antiestrogen can be provided for simultaneous or even for sequential administration. In case of sequential treatment, it is preferred to administer first the antiestrogen and sequentially thereto the antigestagen.

Preferred antiestrogens include tamoxifen, the compounds of EP-A-138,504, especially 7α-[9-(4,4,5,5,5-pentafluoropentylsulfinyl)nonyl]estra-1,3,5(10)-triene-3,17β-diol, the compounds of U.S. Ser. No. 08/915,171 (PCT/EP97/04517), especially 11β-fluoro-7α-(14,14,15,15,15-pentafluoro-6-methyl-10-thia-6-azapentadecyl)-estra-1,3,5 (10)-triene-3,17β-diol, and aromatase inhibitors.

Amounts of antiestrogens are as indicated in the cited texts.

Examined as antigestagens were:
A: 11β-(4-Acetylphenyl)-17β-hydroxy-17α-(1,1,2,2,2-pentafluoroethyl)estr-4-en-3-one (Example 1)
B: 11β-(4-Acetylphenyl)-17β-hydroxy-17α-(1,1,2,2,2-pentafluoroethyl)estra-4,9-dien-3-one (Example 3)
C: 6'-Acetyl-9,11α-dihydro-17β-hydroxy-17α-(1,1,2,2,2-pentafluoroethyl)-4'H-naphth[3',2',1':10,9,11]estr-4-en-3-one (Example 5)
D: 11β-[4-(Dimethylamino)phenyl]-17β-hydroxy-17α-(1-propinyl)estra-4,9-dien-3-one (RU 38 486)
E: 11β-(4-Acetylphenyl)-19,24-dinor-17,23-epoxy-17α-chola-4,9,20-trien-3-one (Org 33 628)

The tests below were all performed on rats according to known methods.

Abortive test s.c. and p.o.: See, for example, EP-A 0 283 428.

Androgen test p.o.: Stimulation of the prostate weight with the test compound, vehicle: s.c. benzylbenzoate, castor oil (1+4); p.o. NaCl-myrj; reference compound testosterone propionate. Virtually no stimulation of the prostate weight is observed up to a dose of 10 mg of test compound/animal/day.

Uterus growth test p.o. for estrogenic action: Stimulation of uterus weight with the test compound, vehicle: s.c. benzylbenzoate/castor oil (1+4); p.o. NaCl-myrj; 3-day treatment of ovariectomized animals; parameters: uterus weight and endometrial epithelium height; vaginal smear negative; reference compound: estradiol 0.1 μg.

Antithymolysis test p.o. on antiglucocorticoid action: See, for example, EP-A 0 283 428.

|  | Compound A | Compound B | Compound C | Compound D | Compound E |
|---|---|---|---|---|---|
| Abortive test on rats s.c., dose [mg/animal/day] (n abortion/n total) | 0.3 (4/4) 0.1 (4/4) 0.03 (4/4) | 0.3 (4/4) 0.1 (4/4) 0.03 (4/4) | 0.3 (4/4) 0.1 (4/4) 0.03 (4/4) | 3 (4/4) 1 (3/4) 0.3 (0/6) | 0.3 (4/4) 0.1 (3/4) 0.03 (0/4) |
| Abortive test on rats p.o. dose [mg/animal/day] (n abortion/n total) | 0.3 (4/4) 0.1 (4/4) 0.03 (4/4) | 0.3 (4/4) 0.1 (4/4) 0.03 (4/4) | 0.3 (4/4) 0.1 (4/4) 0.03 (4/4) 0.01 (4/4) 0.003 (4/4) | 3 (4/4) 1 (2/4) 0.3 (0/4) | 0.3 (4/4) 0.1 (4/4) 0.03 (0/4) |
| Androgen test on rats p.o. dose [mg/animal/day] (% prostate stimulation) | 3 (3.3) 1 (4.8) | 3 (0) 1 (2.1) | n.d. | 10 (7.2) 3 (2.9) 1 (1.6) | 10 (4.4) 3 (5.6) 1 (4.0) |
| Uterus growth test on rats p.o. dose [mg/animal/day] | 10 (3.7) | 10 (2.6) | 10 (4.4) | 10 (6.4) | 10 (2.4) 3 (1.3) |

-continued

|  | Compound A | Compound B | Compound C | Compound D | Compound E |
|---|---|---|---|---|---|
| (% uterus weight stimulation) |  |  |  |  |  |
| Antithymolysis test on rats p.o. | 10 (11.5) | 10 (18.2) | 22 (18.8) | 10 (76) | 10 (44.7) |
| dose [mg/animal/day] | 3 (7.4) | 3 (21.6) | 6.7 (31.6) | 3 (79) | 3 (19.1) |
| (% elimination of dexamethasone-induced thymus suppression) | 1 (6.0) | 1 (1.2) | 2.2 (7.2) | 1 (19) | 1 (4.3) | n.d.: not determined

The invention thus also relates to pharmaceutical agents that are based on pharmaceutically compatible compounds of general formula I, i.e., compounds that are nontoxic in the doses used, optionally in connection with an antiestrogen together with commonly used adjuvants and vehicles.

Finally, this invention also relates to the use of compounds of general formula I, optionally together with an antiestrogen, for the production of pharmaceutical agents. The compounds according to the invention can be processed into pharmaceutical preparations for enteral, percutaneous, parenteral or local administration according to galenical methods that are known in the art. They can be administered in the form of tablets, coated tablets, gel capsules, granulates, suppositories, implants, injectable sterile aqueous or oily solutions, suspensions or emulsions, ointments, creams and gels or by means of intravaginal (e.g., vaginal rings) or intrauterine systems (pessaries, spirals).

The active ingredient or active ingredients can be mixed in this case with the adjuvants that are commonly used in galenicals, such as, e.g., gum arabic, talc, starch, mannitol, methyl cellulose, lactose, surfactants such as Tweens or Myrj, magnesium stearate, aqueous or non-aqueous vehicles, paraffin derivatives, wetting agents, dispersing agents, emulsifiers, preservatives and flavoring substances for taste correction (e.g., ethereal oils).

A dosage unit contains, e.g., about 0.1–100 mg of active ingredient(s). The dosage of the compounds according to the invention is approximately 0.1–400 mg per day in humans. Particular dosages in a given patient can be determined routinely, e.g., considering the usual factors such as patient condition, age, weight, etc. Administration of the compounds is analogous to that of known antigestagens, e.g., RU 486.

The examples below are used to provide a more detailed explanation of this invention:

Without further elaboration, it is believed that one skilled in the art can, using the preceding description, utilize the present invention to its fullest extent. The following preferred specific embodiments are therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 197 06 061.7, filed Feb. 7, 1997, are hereby incorporated by reference.

EXAMPLE 1

11β-(4-Acetylphenyl)-17β-hydroxy-17α-(1,1,2,2,2-pentafluoroethyl)estr-4-en-3-one 1a) 3,3;17,17-Bis[1,2-ethanediybis(oxy)]-11β-[4-[[(1,1,2,2,3,3,4,4,4-nonafluorobutyl)-sulfonyl]oxy]phenyl]estr-5-ene 9.2 ml of a 1.6 molar solution of butyllithium in hexane is added to a solution of 6 g of 4-[3,3;17,17-bis[1,2-ethanediylbis(oxy)]estr-5-en-11β-yl]phenol, whose production is described in WO 91/18917 and WO 91/18918, in 100 ml of absolute tetrahydrofuran at 0° C. It is allowed to stir, for 30 more minutes at 0° C., and then 5 ml of 1,1,2,2,3,3,4,4,4-nonafluoro-1-butanesulfonyl fluoride is added. It is stirred for one more hour at 0° C. Then, the reaction mixture is poured onto saturated aqueous sodium bicarbonate solution. It is extracted with ethyl acetate, washed with saturated aqueous sodium chloride solution, dried on sodium sulfate and evaporated to dryness in a vacuum. Column chromatography of the crude product on silica gel with a mixture of hexane/ethyl acetate yields 8.2 g of 1a) as a white foam.

$^1$H-NMR (CDCl$_3$): δ=7.45 d (J=9 Hz, 2H, aryl); 7.17 d (J=9 Hz, 2H, aryl); 5.55 dbr (J=5 Hz, 1H, H-6); 4.00–3.80 m (8H, ketal); 3.50 ddbr (J=7 Hz+5 Hz, 1H, H-11); 0.53 s (3H, H-18).

1b) 3,3-[1,2-Ethanediylbis(oxy)]-11β-[4-[[(1,1,2,2,3,3,4,4,4-nonafluorobutyl)sulfonyl]oxy]phenyl]estr-5-en-17-one 8.2 g of the compound that is described under 1a) is stirred with 22 g of silica gel and 2 ml of saturated aqueous oxalic acid solution in 85 ml of dichloromethane for 5 hours at room temperature. Then, it is filtered on Celite. It is concentrated by evaporation in a vacuum, and the crude product is purified by crystallization from diisopropyl ether. 5.3 g of 1b) is obtained as white crystals.

$^1$H-NMR (CDCl$_3$): δ=7.45 d (J=9 Hz, 2H, aryl); 7.19 d (J=9 Hz, 2H, aryl); 5.59 dbr (J=5 Hz, 1H, H-6); 4.00–3.88 m (4H, ketal); 3.52 ddbr (J=7 Hz+5 Hz, 1H, H-11); 0.55 s (3H, H-18).

1c) 3,3-[1,2-Ethanediylbis(oxy)]-11β-[4-[[(1,1,2,2,3,3,4,4,4-nonafluorobutyl)sulfonyl]oxy]phenyl]-17α-(1,1,2,2,2-pentafluoroethyl)estr-5-en-17β-ol 1 ml of condensed pentafluoroethyl iodide is mixed with a solution of 691 mg of 1b) in 10 ml of absolute diethyl ether at −0.78° C. 4.77 ml of a 1.5 molar solution of methyllithium-lithium bromide complex in diethyl ether is added at this temperature. Then, it is stirred for one more hour at −78° C. Then, the reaction mixture is poured onto saturated aqueous sodium bicarbonate solution. It is extracted with ethyl acetate, washed with saturated aqueous sodium chloride solution, dried on sodium sulfate and concentrated by evaporation in a vacuum. Chromatography of the crude product that is obtained on silica gel with a mixture of hexane/ethyl acetate yields 719 mg of 1c) as a white foam.

$^1$H-NMR (CDCl$_3$): δ=7.45 d (J=9 Hz, 2H, aryl); 7.19 d (J=9 Hz, 2H, aryl); 5.54 dbr (J=5 Hz, 1H, H-6); 3.88–4.00 m (4H, ketal); 3.53 ddbr (J=7 Hz+5 Hz, 1H, H-11); 0.60 s (3H, H-18).

1d) 11β-(4-Acetylphenyl)-3,3-[1,2-ethanediylbis(oxy)]-17α-(1,1,2,2,2-pentafluoroethyl)estr-5-en-17β-ol A solution of 719 mg of 1c), 0.45 ml of (1-ethoxyethenyl)tributylstannane, 41 mg of tetrakis(triphenylphosphine)palladium(0), 263 mg of lithium chloride and 0.1 ml of pyridine in 12 ml of dioxane is refluxed for 1.5 hours. Then, the reaction mixture is poured onto water. It is extracted with ethyl acetate, and saturated aqueous ammonium chloride solution as well as 3 ml of saturated aqueous oxalic acid solution are added to the organic phase. It is stirred for 30 more minutes at room temperature. Then, the organic phase is separated and washed with saturated aqueous sodium bicarbonate solution as well as with saturated aqueous sodium chloride solution. It is dried on sodium sulfate and concentrated by evaporation in a vacuum. Column chromatography of the crude product that is obtained on silica gel with a mixture of hexane/ethyl acetate yields 440 mg of 1d).

$^1$H-NMR (CDCl$_3$): δ=7.88 d (J=9 Hz, 2H, aryl); 7.47 d (J=9 Hz, 2H, aryl); 5.55 dbr (J=5 Hz, 1H, H-6); 3.88–4.00 m (4H, ketal); 3.55 ddbr (J=7 Hz+5 Hz, 1H, H-11); 2.61 s (3H, acetyl); 0.62 s (3H, H-18).

1e) 11β-(4-Acetylphenyl)-17β-hydroxy-17α-(1,1,2,2,2-pentafluoroethyl)estr-4-en-3-one 440 mg of 1d) is dissolved in 10 ml of acetone. 1 ml of 4N aqueous hydrochloric acid is added, and it is stirred for 1.5 more hours at room temperature. Then, the reaction mixture is poured onto saturated sodium bicarbonate solution. It is extracted with dichloromethane, the organic phase is washed with saturated aqueous sodium chloride solution, dried on sodium sulfate and concentrated by evaporation in a vacuum. Column chromatography of the crude product that is obtained on silica gel with a mixture of hexane/ethyl acetate yields 311 mg of 1e) as a white foam.

$^1$H-NMR (CDCl$_3$): δ=7.89 d (J=9 Hz, 2H, aryl); 7.53 d (J=9 Hz, 2H, aryl); 5.89 sbr (1H, H-4); 3.50 ddbr (J=7 Hz+5 Hz, 1H, H-11); 2.84 m (1H, H-10); 2.60 s (3H, acetyl); 0.70 s (3H, H-18).

EXAMPLE 2

11β-(4-Acetylphenyl)-17β-hydroxy-17α-(1,1,2,2,3,3,4,4,4-nonafluorobutyl)estr-4-en-3-one

2a) 3,3-[1,2-Ethanediylbis(oxy)]-17α-(1,1,2,2,3,3,4,4,4-nonafluorobutyl)-11β-[4-[[(1,1,2,2,3,3,4,4,4-nonafluorobutyl)sulfonyl]oxy]phenyl]estr-5-en-17β-ol Analogously to Example 1c), 691 mg of 1b) in 15 ml of absolute diethyl ether is reacted with the reagent that is formed from 0.52 ml of 1-iodo-1,1,2,2,3,3,4,4,4-nonafluorobutane and 1.67 ml of a 1.5 molar solution of a methyllithium-lithium bromide complex in diethyl ether. After chromatography on silica gel with a mixture of hexane/ethyl acetate, 838 mg of 2a) is obtained as a white foam.

$^1$H-NMR (CDCl$_3$): δ=7.44 d (J=9 Hz, 2H, aryl); 7.18 d (J=9 Hz, 2H, aryl); 5.55 dbr (J=5 Hz, 1H, H-6); 3.88–4.00 m (4H, ketal); 3.53 ddbr (J=7 Hz+5 Hz, 1H, H-11); 0.61 s (3H, H-18).

2b) 11β-(4-Acetylphenyl)-3,3-[1,2-ethanediylbis(oxy)]-17α-(1,1,2,2,3,3,4,4,4-nonafluorobutyl)estr-5-en-17β-ol Analogously to Example 1d), 838 mg of 2a) is reacted with 0.46 ml of (1-ethoxyethenyl)tributylstannane, 43 mg of tetrakis(triphenylphosphine)palladium(0), 272 mg of lithium chloride and 0.1 ml of pyridine in 12 ml of dioxane. After working-up as well as treatment with saturated aqueous ammonium chloride solution as well as saturated aqueous oxalic acid solution and column chromatography on silica gel with a mixture of hexane/ethyl acetate, 505 mg of 2b) is obtained as a white foam.

$^1$H-NMR (CDCl$_3$): δ=7.85 d (J=9 Hz, 2H, aryl); 7.46 d (J=9 Hz, 2H, aryl); 5.55 dbr (J=5 Hz, 1H, H-6); 3.88–4.00 m (4H, ketal); 3.55 ddbr (J=7 Hz+5 Hz, 1H, H-11); 2.61 s (3H, acetyl); 0.63 s (3H, H-18).

2c) 11β-(4-Acetylphenyl)-17β-hydroxy-17α-(1,1,2,2,3,3,4,4,4-nonafluorobutyl)estr-4-en-3-one Analogously to Example 1e), 505 mg of 2b) is reacted with 4N hydrochloric acid in acetone. After column chromatography on silica gel, with a mixture of hexane/ethyl acetate, 372 mg of 2c) is obtained as a white foam.

$^1$H-NMR (CDCl$_3$): δ 7.89 d (J=9 Hz, 2H, aryl); 7.55 d (J=9 Hz, 2H, aryl); 5.88 sbr (1H, H-4); 3.51 ddbr (J=7 Hz+5 Hz, 1H, H-11); 2.85 m (1H, H-10); 2.60 s (3H, acetyl); 0.70 s (3H, H-18).

EXAMPLE 3

11β-(4-Acetylphenyl)-17β-hydroxy-17α-(1,1,2,2,2-pentafluoroethyl)estra-4,9-dien-3-one

3a) 3,3-[2,2-Dimethyl-1,3-propanediylbis(oxy)]-17α-(1,1,2,2,2-pentafluoroethyl)-11β-[4-(2,5,5-trimethyl-1,3-dioxolan-2-yl)phenyl]-5α-estr-9-ene-5,17β-diol Analogously to Example 1c), 1.08 g of 3,3-[2,2-dimethyl-1,3-propanediylbis(oxy)]-5-hydroxy-11β-[4-(2,5,5-trimethyl-1,3-dioxolan-2-yl)phenyl]-5α-estr-9-en-17-one, whose production is described in EP 0190759, Example 6c) is described, is reacted in 19 ml of absolute diethyl ether with the reagent that is formed from 1.9 ml of 1-iodo-1,1,2,2,2-pentafluoroethane and 8.7 ml of a 1.5 molar solution of methyllithium-lithium bromide complex in diethyl ether. After column chromatography on silica gel with a mixture of hexane/ethyl acetate, 644 mg of the title compound is obtained as a colorless foam.

$^1$H-NMR (CDCl$_3$): δ=7.29 d (J=9 Hz, 2H, aryl); 7.23 d (J=9 Hz, 2H, aryl); 4.42 s (1H, 5-OH); 4.35 dbr (J=7 Hz, 1H, H-11); 1.52 s (3H, arylketal); 1.26 s (3H, arylketal); 1.04 s (3H, 3-ketal); 0.89 s (3H, 3-ketal); 0.57 s (3H, arylketal); 0.51 s (3H, H-18).

3b) 11β-(4-Acetylphenyl)-17β-hydroxy-17α-(1,1,2,2,2-pentafluoroethyl)estra-4,9-dien-3-one 635 mg of the compound that is described under 3a) is stirred in 9 ml of methanol with 0.4 ml of aqueous semi-concentrated sulfuric acid for two hours at room temperature. Then, it is poured onto saturated aqueous sodium bicarbonate solution and extracted with ethyl acetate. The organic phase is washed with saturated aqueous sodium chloride solution, dried on sodium sulfate, filtered and concentrated by evaporation in a vacuum. Column chromatography on silica gel with a mixture of hexane/ethyl acetate yields 428 mg of the title compound as a colorless foam.

Flash point: 260.4° C. (diisopropyl ether), [α]$^{22}_D$=+181.3° (CHCl$_3$, c=0.535)

EXAMPLE 4

11β-(4-Acetylphenyl)-17β-hydroxy-17α-(1,1,2,2,2-pentafluoroethyl)estra-4,9,15-trien-3-one 4a) 3,3-[2,2-Dimethyl-1,3-propanediylbis(oxy)]-17α-(1,1,2,2,2-pentafluoroethyl)-11β-[4-(2,5,5-trimethyl-1,3-dioxolan-2-yl-phenyl]-5α-estra-9,15-diene-5,17β-diol Analogously to Example 1c), 1.15 g of 3,3-[2,2-dimethyl-1,3-propanediylbis(oxy)]-5-hydroxy-11β-[4-(2,5,5-trimethyl-1,3-dioxolan-2-yl)phenyl]-5α-estra-9,15-dien-17-one, whose production is described in WO 89/00578, Example 1b), in 20 ml of absolute diethyl ether and 10 ml of absolute tetrahydrofuran is reacted with the reagent that is formed from 2.0 ml of 1-iodo-1,1,2,2,2-pentafluoroethane and 9.3 ml of a 1.5 molar solution of methyllithium-lithium bromide complex in diethyl ether. After column chromatography on silica gel with a mixture of hexane/ethyl acetate, 1.16 g of the title compound is obtained as a colorless foam.

$^1$H-NMR (CDCl$_3$): δ=7.31 d (J=9 Hz, 2H, aryl); 7.24 d (J=9 Hz, 2H, aryl); 6.31 dbr (J=6 Hz, 1H, H-15); 5.58 dddbr (J=6 Hz+3.5 Hz+1.5 Hz, 1H, H-16); 4.49 s (1H, 5-OH); 4.40 dbr (J=8 Hz, 1H, H-11); 1.52 s (3H, arylketal); 1.26 s (3H, arylketal); 1.03 s (3H, 3-ketal); 0.89 s (3H, 3-ketal); 0.68 s (3H, H-18); 0.58 s (3H, arylketal).

4b) 11β-(4-Acetylphenyl)-17β-hydroxy-17α-(1,1,2,2,2-pentafluoroethyl)estra-4,9,15-trien-3-one Analogously to the process that is described in 3b), 1.15 g of the compound that is described under 4a) is reacted in 16.5 ml of methanol with 0.73 ml of aqueous semiconcentrated sulfuric acid to 572 mg of the title compound as a colorless foam.

Flash point: 213.9° C. (diisopropyl ether), [α]$^{22}_D$=+210.5° (CHCl$_3$, c=0.615).

EXAMPLE 5

9,11α-Dihydro-6'-(4-fluorophenyl)-17β-hydroxy-17α-(1,1,2,2,2-pentafluoroethyl)-4'H-naphth[3',2',1':10,9,11]estr-4-en-3-one 5a) 9,11α-Dihydro-3,3-[2,2-dimethyl-1,3-propanediylbis(oxy)]-6'-[[(1,1,2,2,3,3,4,4,4-nonafluorobutyl)sulfonyl]oxy]-17α-(1,1,2,2,2-pentafluoroethyl)-4'H-naphth[3',2',1':10,9,11]-5α-estrane-5,17β-diol The solution of about 4 ml of pentafluoroethyliodide in 20 ml of anhydrous ether is mixed at −78° C. under an atmosphere of dry argon with 13.4 ml of a 1.7 molar solution of tert-butyllithium in hexane, and it is stirred for 30 minutes. Then, the solution of 2.0 g (2.62 mmol) of 9,11α-dihydro-3,3-[2,2-dimethyl-1,3-propanediylbis(oxy)]-5-hydroxy-6'-[[(1,1,2,2,3,3,4,4,4-nonafluorobutyl)sulfonyl] oxy]-4'H-naphth[3',2',1':10,9,11]-5α-estran-17-one, which has been produced analogously to the process that is described in DE 4216003 (Example 1b), in 60 ml of anhydrous toluene is added in drops and allowed to heat to −10° C. within 2 hours. It is poured into a saturated aqueous sodium bicarbonate solution, extracted several times with ethylacetate, the combined organic extracts are washed with a saturated aqueous sodium chloride solution and dried on sodium sulfate. The residue that is obtained after filtration and removal of the solvent is purified by chromatography on about 300 ml of fine silica gel with a gradient system of hexane and ethyl acetate. 1.40 g (1.59 mmol, 61%) of the title compound is isolated as a colorless solid as well as 730 mg (0.96 mmol, 36%) of starting material.

$^1$H-NMR (CDCl$_3$): δ=0.41 (3H), 0.93 (3H), 1.00 (3H), 1.20–1.36 (2H), 1.42–1.81 (11H), 1.93 (2H), 2.07–2.28 (3H), 2.31–2.48 (1H), 2.61–2.77 (2H), 3.15 (1H), 3.21 (1H), 3.45–3.65 (4H), 4.48 (1H), 6.98 (1H), 7.04 (1H), 7.47 (1H) ppm.

5b) 9,11α-Dihydro-3,3-[2,2-dimethyl-1,3-propanediylbis(oxy)]-6'-(4-fluorophenyl)-17α-(1,1,2,2,2-pentafluoroethyl)-4'H-naphth[3',2',1':10,9,11]-5α-estrane-5,17β-diol The solution of 400 mg (453 μmol) of the compound that is presented according to Example 5a is mixed in a mixture of 7 ml of anhydrous toluene and 3 ml of anhydrous ethanol in succession with 43 mg of lithium chloride, 0.66 ml of a 2M sodium carbonate solution, 82 mg of (4-fluorophenyl) boronic acid, and 50 mg of tetrakis(triphenylphosphine) palladium(O) and heated under an atmosphere of argon for 1.5 hours to 95° C. The reaction mixture is diluted with water, extracted with ethyl acetate, the combined organic extracts are washed with a saturated aqueous sodium chloride solution and dried on sodium sulfate. The residue that is obtained after filtration and removal of the solvent is purified by chromatography on about 150 ml of fine silica gel with a gradient system of hexane and ethyl acetate. 264 mg (389 μmol, 86%) of the title compound is isolated as a colorless solid.

$^1$H-NMR (CDCl$_3$): δ=0.49 (3H), 0.93 (3H), 0.99 (3H), 1.21–2.28 (18H), 2.30–2.47 (1H), 2.76 (2H), 3.17 (1H), 3.26 (1H), 3.47–3.66 (4H), 4.48 (1H), 7.11 (2H), 7.23 (1H), 7.33 (1H), 7.45 (1H), 7.54 (2H) ppm.

5c) 9,11α-Dihydro-6'-(4-fluorophenyl)-17-hydroxy-17α-17α-(1,1,2,2,2-pentafluoroethyl)-4'H-naphth[3',2'1':10,9,11α-estr-4-en-3-one The solution of 260 mg (383 µmol) of the compound, presented according to Example 5b), in 13 ml of acetone is mixed with 700 µl of aqueous 4N hydrochloric acid, and it is heated for 4 hours to 50° C. It is poured into a saturated aqueous sodium bicarbonate solution, extracted several times with dichloromethane, the combined organic extracts are washed with a saturated aqueous sodium chloride solution and dried on sodium sulfate. The residue that is obtained after filtration and removal of the solvent is purified by chromatography on about 100 ml of fine silica gel with a gradient system of hexane and ethyl acetate. 206 mg (359 µmol 94%) of the title compound is isolated as crystalline solid.

$^1$H-NMR (CDCl$_3$): δ=0.55 (3H), 1.22 (1H), 1.33–1.50 (2H), 1.54–1.89 (5H), 1.92–2.54 (8H), 2.66 (1H), 2.81 (1H), 2.87 (1H), 3.31 (1H), 3.43 (1H), 5.90 (1H), 7.12 (2H), 7.27 (1H), 7.37 (1H), 7.45–7.60 (3H) ppm.

EXAMPLE 6

6'-Acetyl-9,11α-dihydro-17β-hydroxy-17α-(1,1,2,2,2-pentafluoroethyl)-4'H-naphth[3',2',1':10,9,11]estr-4-en-3-one The solution of 600 mg (680 µmol) of the compound, presented according to Example 5a), in 7 ml of anhydrous N,N-dimethylformamide is mixed under an atmosphere of dry argon in succession with 69 mg of lithium chloride, 381 µl of (1-ethoxyethenyl)tributylstannane, and 25 mg of tetrakis(triphenylphosphine)palladium(O), and it is heated for 1.5 hours to 110° C. After cooling, it is mixed with 10 ml of acetone, 1.5 ml of aqueous 4N hydrochloric acid, allowed to react for 2 hours at 23° C. and then heated for 3 more hours to 50° C. It is poured into a saturated aqueous sodium bicarbonate solution, extracted several times with dichloromethane, the combined organic extracts are washed with a saturated aqueous sodium chloride solution and dried on sodium sulfate. From the residue that is obtained after filtration and removal of the solvent, 206 mg of the title compound that is still contaminated and that is further purified on 10 analytic thin-layer plates is obtained by crystallization from dichloromethane and acetone. A mixture of hexane and ethyl acetate is used as a mobile solvent; a mixture of dichloromethane and methanol is used as an eluant. 160 mg (306 µmol, 45%) of the title compound is isolated as a colorless solid.

$^1$H-NMR (CDCl$_3$): δ=0.47 (3H), 1.21 (1H), 1.31–1.51 (2H), 1.53–1.85 (5H), 1.98 (2H), 2.12–2.52 (6H), 2.54 (3H), 2.64 (1H), 2.82 (1H), 2.88 (1H), 3.31 (1H), 3.42 (1H), 5.91 (1H), 7.54 (1H), 7.71 (1H), 7.77 (1H) ppm.

EXAMPLE 7

4-[9,11α-Dihydro-17β-hydroxy-3-oxo-17α-(1,1,2,2,2-pentafluoroethyl)-4'H-naphth[3',2',1':10,9,11]estr-4-en-6'-yl]benzonitrile 7a) 4-[9,11α-Dihydro-5,17β-hydroxy-3,3-[2,2-dimethyl-1,3-propanediylbis(oxy)]-17α-(1,1,2,2,2-pentafluoroethyl)-4'H-naphth[3',2',1':10,9,11]-5α-estran-6'-yl]benzonitrile 400 mg (453 µmol) of the compound that is presented according to Example 5b) is reacted analogously to Example 5b) with use of 4-(5,5-dimethyl-1,3,2-dioxaborinan-2-yl) benzonitrile, and after working-up and purification, 301 mg (439 µmol, 97%) of the title compound is isolated as a crystalline solid.

7b) 4-[9,11α-Dihydro-17β-hydroxy-3-oxo-17α-(1,1,2,2,2-pentafluoroethyl)-4'H-naphth[3',2',1':10,9,11]estr-4-en-6'-yl]benzonitrile 296 mg (431 µmol) of the compound that is presented according to Example 7a) is reacted analogously to Example 5c), and after working-up and purification, 228 mg (392 µmol, 91%) of the title compound is isolated as a crystalline solid.

$^1$H-NMR (CDCl$_3$): δ=0.53 (3H), 1.22 (1H), 1.35–1.51 (2H), 1.55–1.88 (5H), 1.92–2.14 (3H), 2.14–2.53 (5H), 2.65 (1H), 2.81 (1H), 2.88 (1H), 3.32 (1H), 3.45 (1H), 5.91 (1H), 7.32 (1H), 7.42 (1H), 7.55 (1H), 7.70 (4H) ppm.

EXAMPLE 8

17β-Hydroxy-11β-(4-hydroxyphenyl)-17α-(1,1,2,2,2)-pentafluoroethyl)estra-4,9-dien-3-one 8a) 3,3-[2,2-Dimethyl-1,3-propanediylbis(oxy)]-5-hydroxy-11β-[4-(phenylmethoxy)phenyl]-5α-estr-9-en-17-one 1.17 g of magnesium chips is introduced under protective gas into 4 ml of absolute tetrahydrofuran and mixed with one drop of 1,2-dibromoethane. After the reaction has set in, a solution of 12.7 g of 1-bromo-4-(phenylmethoxy)benzene (for production, see J. Amer. Chem. Soc. 42, 657 (1920)) in 80 ml of absolute tetrahydrofuran is slowly added in drops. The reaction mixture is refluxed until the magnesium has reacted completely. Then, it is cooled to 0° C., and mixed with 2.39 g of copper(I) chloride. A solution of 3 g of 3,3-[2,2-dimethyl-1,3-propanediylbis(oxy)]-5,10-epoxy-5α,10α-estr-9(11)-en-17-one (for production, see Tetrahedron Lett. 26, 2069–2072 (1985)) in 80 ml of absolute tetrahydrofuran is slowly added in drops. The reaction mixture is stirred overnight at room temperature and then poured onto saturated aqueous ammonium chloride solution. The aqueous phase is extracted with ethyl acetate, the organic phases are combined, washed with saturated aqueous sodium chloride solution and dried on sodium sulfate. It is filtered and concentrated by evaporation in a vacuum. Column chromatography on silica gel with a mixture of hexane/ethyl acetate yields 3.7 g of the title compound as a colorless foam.

$^1$H-NMR (CDCl$_3$): δ=7.50–7.27 m (5H, benzyl); 7.13 d (J=9 Hz, 2H, aryl); 6.88 d (J=9 Hz, 2H, aryl); 5.02 s (2H, benzyl); 4.45 s (1H, 5-OH); 4.27 dbr (J=60.5 Hz, 1H, H-11); 1.06 s (3H, 3-ketal); 0.87 s (3H, 3-ketal); 0.50 s (3H, H-18).

8b) 3,3-(2,2-Dimethyl-1,3-propanediylbis(oxy)]-17α-(1,1,2,2,2-pentafluoroethyl)-11β-[4-(phenylmethoxy)phenyl]-5α-estr-9-ene-5,17β-diol Analogously to Example 1c), 1.35 g of the compound, described under 8a), in 48 ml of absolute toluene is reacted with the reagent that is formed from 1.18 g of 1-iodo-1,1,2,2,2-pentafluoroethane and 2.4 ml of a 1.5 molar solution of methyllithium-lithium bromide complex in diethyl ether. After column chromatography on silica gel with a mixture of hexane/ethyl acetate, 730 mg of the title compound is obtained as a colorless foam.

$^1$H-NMR (CDCl$_3$): δ=7.50–7.30 m (5H, benzyl); 7.12 d (J=9 Hz, 2H, aryl); 6.88 d (J=9 Hz, 2H, aryl); 5.02 s (2H, benzyl); 4.45 s (1H, 5-OH); 4.29 dbr (J=6 Hz, 1H, H-11); 1.06 s (3H, 3-ketal); 0.87 s (3H, 3-ketal); 0.56 s (3H, H-18).

8c) 3,3-[2,2-Dimethyl-1,3-propanediylbis(oxy)]-17α-(1,1,2,2,2-pentafluoroethyl)-11β-(4-hydroxyphenyl)-5α-estr-9-ene-5,17β-diol 730 mg of the compound that is produced under 8b) is dissolved in 11 ml of methanol and mixed with 341 mg of ammonium formate and 73 mg of 10% palladium on activated carbon. The reaction mixture is stirred for two hours at room temperature, then filtered on Celite®. The residue is thoroughly rewashed with ethyl acetate. The filtrate is concentrated by evaporation in a vacuum. 631 mg of compound 8c), which is further reacted untreated, is obtained.

8d) 17β-Hydroxy-11β-(4-hydroxyphenyl)-17α-(1,1,2,2,2-pentafluoroethyl)estra-4,9-dien-3-one 631 mg of the compound that is described under 8c) is reacted analogously to the process that is described in 3b) in 11 ml of methanol with 0.48 ml of aqueous semiconcentrated sulfuric acid to 428 mg of the title compound as a colorless foam.
$^1$H-NMR (CDCl$_3$): δ=7.00 d (J=9 Hz, 2H, aryl); 6.75 d (J=9 Hz, 2H, aryl); 5.94 sbr (1H, OH); 5.80 s (1H, H-4); 4.38 dbr (J=7 Hz, 1H, H-11); 0.61 s (3H, H-18).

EXAMPLE 9

11β-[4-(Acetyloxy)phenyl]-17β-hydroxy-17α-(1,2,2,2-pentafluoroethyl)estra-4,9-dien-3-one 300 mg of the compound that is described under 8d) is dissolved in 12 ml of pyridine and stirred for four hours with 61 μl of acetic anhydride at room temperature. The reaction mixture is poured onto saturated aqueous ammonium chloride solution. The aqueous phase is extracted with ethyl acetate, the organic phases are combined, washed with saturated aqueous sodium chloride solution and dried on sodium sulfate. It is filtered and concentrated by evaporation in a vacuum. Column chromatography on silica gel with a mixture of hexane/ethyl acetate yields 248 mg of the title compound as a colorless foam.
$^1$H-NMR (CDCl$_3$): δ=7.18 d (J=9 Hz, 2H, aryl); 7.02 d (J=9 Hz, 2H, aryl); 5.79 s (1H, H-4); 4.45 dbr (J=6 Hz, 1H, H-11); 2.29 s (3H, acetyl); 0.61 s (3H, H-18).

EXAMPLE 10

17β-Hydroxy-11β-[4-(hydroxymethyl)phenyl]-17α-(1,1,2,2,2-pentafluoroethyl)estra-4,9-dien-3-one

10a) 3,3-[2,2-Dimethyl-1,3-propanediylbis(oxy)]-4-hydroxy-11β-[4-[(methoxymethoxy)methyl]phenyl]-5α-estr-9-en-17-one Analogously to the process described under 8a) and after column chromatography on silica gel with a mixture of hexane/ethyl acetate, 7.14 g of the title compound is obtained as a colorless foam from 6.0 g of 3,3-[2,2-dimethyl-1,3-propanediylbis(oxy)]-5,10-epoxy-5α,10α-estr-9(11)-en-17-one in 160 ml of absolute tetrahydrofuran, 22.32 g of 1-bromo-4-[(methoxymethoxy)methyl]benzene (for production, see Synth. Commun. 20, 1469–1472 (1990)) in 160 ml of absolute tetrahydrofuran, 2.35 g of magnesium chips in 10 ml of absolute tetrahydrofuran and 4.78 g of copper (I) chloride.
$^1$H-NMR (CDCl$_3$): δ=7.27 d (J=9 Hz, 2H, aryl); 7.24 d (J=9 Hz, 2H, aryl); 4.72 s (2H, acetal); 4.56 s (2H, benzyl); 4.48 s (1H, 5-OH); 4.33 dbr (J=6.5 Hz, 1H, H-11); 3.42 s (3H, methoxy); 1.07 s (3H, 3-ketal); 0.87 s (3H, 3-ketal); 0.49 s (3H, H-18).

10b) 3,3-[2,2-Dimethyl-1,3-propanediylbis(oxy)-17α-(1,1,2,2,2-pentafluoroethyl)-11β-(4-[(methoxymethoxy)methyl]phenyl]-5α-estr-9-ene-5,17β-diol Analogously to Example 1c), 4.85 g of the compound, described under 10a), in 200 ml of absolute toluene is reacted with the reagent that is formed from 18.2 g of 1-iodo-1,1,2,2,2-pentafluoroethane and 43.3 ml of a 1.5 molar solution of methyllithium-lithium bromide complex in diethyl ether. After column chromatography on silica gel with a mixture of hexane/ethyl acetate, 4.13 g of the title compound is obtained as a colorless foam.
$^1$H-NMR (CDCl$_3$): δ=7.25 d (J=9 Hz, 2H, aryl); 7.20 d (J=9 Hz, 2H, aryl); 4.71 s (2H, acetal); 4.54 s (2H, benzyl); 4.46 s (1H, 5-OH); 4.32 dbr (J=6 Hz, 1H, H-11); 3.41 s (3H, methoxy); 1.06 s (3H, 3-ketal); 0.86 s (3H, 3-ketal); 0.52 s (3H, H-18).

10c) 17β-Hydroxy-11β-[4-(hydroxymethyl)phenyl]-17α-(1,1,2,2,2-pentafluoroethyl)estra-4,9-dien-3-one 4.13 g of the compound that is described under 10b) is reacted analogously to the process that is described in 3b) in 65 ml of methanol with 2.84 ml of aqueous semiconcentrated sulfuric acid to 2.26 g of the title compound as a colorless foam.
$^1$H-NMR (CDCl$_3$): δ=7.27 d (J=9 Hz, 2H, aryl); 7.17 d (J=9 Hz, 2H, aryl); 5.78 s (1H, H-4); 4.64 s (2H, benzyl); 4.45 dbr (J=6.5 Hz, 1H, H-11); 0.59 s (3H, H-18).

EXAMPLE 11

4-[17β-Hydroxy-3-oxo-17α-(1,1,2,2,2-pentafluoroethyl)estra-4,9-dien-11β-yl]benzaldehyde 497 mg of the compound that is produced under 10c) is stirred with 431 mg of pyridinium chlorochromate in 10 ml of dichloromethane for two hours at room temperature, then it is filtered with silica gel. The residue is thoroughly rewashed with ethyl acetate. The filtrate is concentrated by evaporation in a vacuum. After column chromatography on silica gel with a mixture of hexane/ethyl acetate, 415 mg of the title compound is obtained as a colorless foam.
$^1$H-NMR (CDCl$_3$): δ=9.97 s (H, formyl); 7.81 d (J=9 Hz, 2H, aryl); 7.39 d (J=9 Hz, 2H, aryl); 5.81 s (1H, H-4); 4.52 dbr (J=7 Hz, 1H, H-11); 0.58 s (3H, H-18).

EXAMPLE 12

4-[17β-Hydroxy-3-oxo-17α-(1,1,2,2,2-pentafluoroethyl)estra-4,9-dien-11β-yl]benzoic acid methyl ester A solution of 125 mg of the compound, produced under 11), in 2.5 ml of methanol is added to 81.4 mg of potassium cyanide in 1.25 ml of methanol. 390 mg of manganese(IV) oxide and 22 ml of glacial acetic acid are added to the reaction mixture, which then is stirred for one hour at room temperature. It is filtered with Celite®, the filtrate is taken up in ethyl acetate/water, and the aqueous phase is extracted with ethyl acetate. The combined organic phases are washed with water and saturated aqueous sodium chloride solution, dried on sodium sulfate, filtered and concentrated by evaporation in a vacuum. After column chromatography on silica gel with a mixture of hexane/ethyl acetate, 120 mg of the title compound is obtained as a colorless foam.
$^1$H-NMR (CDCl$_3$): δ=7.94 d (J=9 Hz, 2H, aryl); 7.27 d (J=9 Hz, 2H, aryl); 5.79 s (1H, H-4); 4.49 dbr (J=6 Hz, 1H, H-11); 3.89 s (3H, methoxy) 0.57 s (3H, H-18).

EXAMPLE 13

17β-Hydroxy-11β-[4-(1-hydroxyethyl)phenyl]-17α-(1,1,2,2,2-pentafluoroethyl)estra-4,9-dien-3-one

13a) 3,3-[2,2-Dimethyl-1,3-propanediylbis(oxy)]-5-hydroxy-11β-[4-[1-[(tetrahydro-2H-pyran-2-yl)oxy]ethyl]phenyl]-5α-estr-9-en-17-one Analogously to the process described under 8a) and after column chromatography on silica gel with a mixture of hexane/ethyl acetate, 2.06 g of the title compound is obtained as a diastereomer mixture in the acetal and the benzyl positions from 1.6 g of 3,3-[2,2-dimethyl-1,3-propanediylbis(oxy)]-5,10-epoxy-5α,10α-estr-9(11)-en-17-one in 40 ml of absolute tetrahydrofuran, 7.4 g of 2-[1-(4-bromophenyl)ethoxy]tetrahydro-2H-pyran (for production see Arzneim. Forsch. 25, 1495–1501 (1975)) in 40 ml of absolute tetrahydrofuran, 1.3 g of magnesium chips in 2 ml of absolute tetrahydrofuran and 1.3 g of copper (I) chloride.

$^1$H-NMR (CDCl$_3$): δ=7.28 d (J=9 Hz, 2H, aryl); 7.18 d (J=9 Hz, 2H, aryl); 4.90–4.72 m (2H, acetal and benzyl ether); 4.44 s (1H, 5-OH); 4.30 dbr (J=6.5 Hz, 1H, H-11); 1.45/1.42 d (J=6 Hz, 3H, methyl); 1.05 s (3H, 3-ketal); 0.87 s (3H, 3-ketal); 0.46 s (3H, H-18).

13b) 3,3-[2,2-Dimethyl-1,3-propanediylbis(oxy)]-17α-(1,1,2,2,2-pentafluoroethyl)-11β-[4-[1-[(tetrahydro-2H-pyran-2-yl)oxy]ethyl]-phenyl]-5α-estr-9-ene-5,17β-diol Analogously to Example 1c), 1.45 g of the compound, described under 13a), in 50 ml of absolute toluene is reacted with the reagent that is formed from 4.9 g of 1-iodo-1,1,2,2,2-pentafluoroethane and 11.7 ml of a 1.5 molar solution of methyllithium-lithium bromide complex in diethyl ether. After column chromatography on silica gel with a mixture of hexane/ethyl acetate, 1.22 g of the title compound is obtained as a diastereomeric mixture in the acetyl and benzyl positions.

$^1$H-NMR (CDCl$_3$): δ=7.28 d (J=9 Hz, 2H, aryl); 7.18 d (J=9 Hz, 2H, aryl); 4.90–4.74 m (2H), acetal and benzylether); 4.42 s (1H, 5-OH); 4.31 dbr (J=6.5 Hz, 1H, H-11); 1.46/1.42 d (J=6 Hz, 3H, methyl); 1.05 s (3H, 3-ketal); 0.87 s (3H, 3-ketal); 0.51 s (3H, H-18).

13c) 17β-Hydroxy-11β-[4-(1-hydroxyethyl)phenyl]-17α-(1,1,2,2,2-pentafluoroethyl)estra-4,9-dien-3-one Analogously to the process that is described in 3b), 1.22 g of the compound that is described under 13b) is reacted in 18 ml of methanol with 778 μl of aqueous semiconcentrated sulfuric acid to 693 mg of the title compound as a colorless foam. An epimer mixture is obtained on benzylcarbinol.

$^1$H-NMR (CDCl$_3$): δ=7.28 d (J=9 Hz, 2H, aryl); 7.15 d (J=9 Hz, 2H, aryl); 5.79 s (1H, H-4); 4.88 qbr (J=6 Hz, 1H, benzyl); 4.45 dbr (J=6 Hz, 1H, H-11); 1.49 d (J=6 Hz, 3H, methyl); 0.60 s (3H, H-18).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for treating a gynecological myoma comprising administering to a human in need thereof an antigestagenically effective amount of a 17α-fluoroalkyl steroid of general formula I

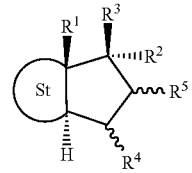

in which

R$^1$ stands for a methyl or ethyl group,

R$^2$ stands for a radical of formula C$_n$F$_m$H$_o$, whereby n is 2, 3, 4, 5 or 6, m>1 and m+o=2n+1, R$^3$ stands for a free etherified or esterified hydroxy group, R$^4$ and R$^5$ each stand for a hydrogen atom, together for an additional bond or a methylene group, St stands for a steroidal ABC-ring system of partial formula A, B or C

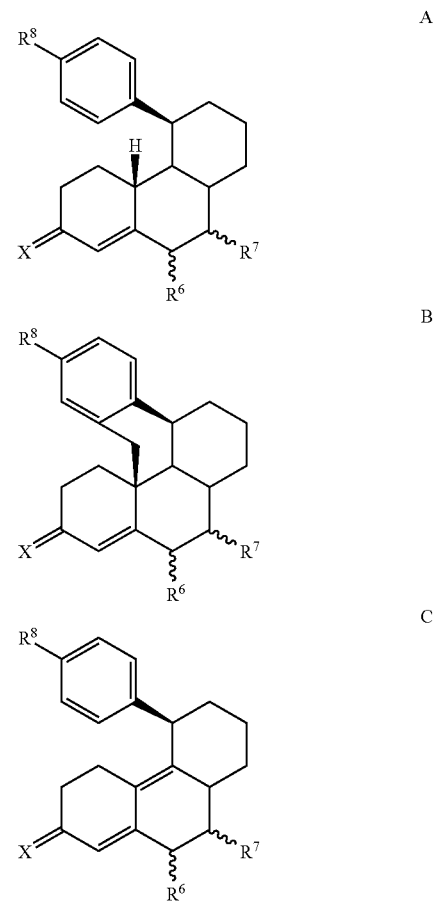

in which

R$^6$ means a hydrogen atom, a straight-chain C$_1$–C$_4$ alkyl group or branched C$_3$–C$_4$ alkyl group or a halogen atom, R⁷ means a hydrogen atom, a straight-chain $C_1$–$C_4$ alkyl group or a branched $C_3$–$C_4$ alkyl group, or if St stands for a steroidal ABC-ring system A or B, in addition R⁶ and R⁷ together mean an additional bond, X means an oxygen atom, a hydroxyimino grouping =N—OH or two hydrogen atoms, R⁸ means a radical Y or an aryl radical that is optionally substituted in several places with a group Y, whereby Y is a hydrogen atom, a halogen atom, an —OH, —NO₂, —N₃, —CN, —NR⁹ᵃR⁹ᵇ, —NHSO₂R⁹, —CO₂R⁹, $C_1$–$C_{10}$ alkyl, $C_1$–$C_{10}$ alkoxy, $C_1$–$C_{10}$ alkanoyloxy, benzoyloxy, $C_1$–$C_{10}$ alkanoyl, $C_1$–$C_{10}$ hydroxyalkyl or benzoyl group, and R⁹ᵃ and R⁹ᵇ are the same or different and represent a hydrogen atom or a $C_1$–$C_{10}$ alkyl group, and R⁹ is a hydrogen atom or a $C_{1-10}$ alkyl group, or for a —NR⁹ᵃR⁹ᵇ radical, also a physiologically compatible salt thereof with an acid, or for a —CO₂R⁹ radical in which R⁹ is hydrogen, also a physiologically compatible salt thereof with a base.

2. A method according to claim 1, in which St stands for a steroidal ring system of partial formula A.

3. A method according to claim 1, in which St stands for a steroidal ring system of partial formula B.

4. A method according to claim 1, in which St stands for a steroidal ring system of partial formula C.

5. A method according to claim 1, in which n=2, 3 or 4.

6. A method according to claim 5, in which o=0.

7. A method according to claim 6, in which n=2.

8. A method according to claim 1, in which R³ is a free hydroxy group.

9. A method according to claim 1, in which R⁸ stands for radical Y.

10. A method according to claim 9, in which Y stands for a $C_1$–$C_{10}$ alkanoyl group.

11. A method according to claim 10, in which Y stands for a formyl, acetyl or propionyl group.

12. A method according to claim 9, in which Y stands for a $C_1$–$C_{10}$ hydroxyalkyl group.

13. A method according to claim 12, in which y stands for a hydroxymethyl or 1-hydroxyethyl group.

14. A method according to claim 9, in which Y stands for a hydroxy group.

15. A method according to claim 9, in which Y stands for an acetyloxy group.

16. A method according to claim 9, in which Y stands for a methoxycarbonyl group.

17. A method according to claim 1, in which R⁸ stands for an aryl radical that is substituted with a group Y.

18. A method according to claim 17, in which the aryl radical is a phenyl, naphthalinyl, furanyl, benzofuranyl, thienyl or pyridinyl radical.

19. A method according to claim 18, in which R⁸ is a 4-cyanophenyl radical.

20. A method according to claim 18, in which R⁸ is a 4-halophenyl radical.

21. A method according to claim 20, in which R⁸ is a 4-fluorophenyl radical.

22. A method according to claim 1, in which R⁴ and R⁵ each stand for a hydrogen atom.

23. A method according to claim 1, in which R⁴ and R⁵ together stand for an additional bond.

24. A method according to claim 1, in which R⁶ and R⁷ are each a hydrogen atom.

25. A method according to claim 1, wherein said steroid is

11β-(4-Acetylphenyl)-17β-hydroxy-17α-(1,1,2,2,2-pentafluoroethyl)estr-4-en-3-one;

4'-[17β-hydroxy-3-oxo-17α-(1,1,2,2,2-pentafluoroethyl)estr-4-en-11β-yl][1,1'-biphenyl]4-carbonitrile;

11β-(4'-fluoro[1,1'-biphenyl]-4-yl)-17β-hydroxy-17α-(1,1,2,2,2-pentafluoroethyl)estr-4-en-3-one;

17β-hydroxy-17α-(1,1,2,2,2-pentafluoroethyl)-11β-[4-(3-pyridinyl)phenyl]estr-4-en-3-one;

11β-(4-acetylphenyl)-17β-hydroxy-17α-(1,1,2,2,2-pentafluoroethyl)estra-4,15-dien-3-one;

4'-[17β-hydroxy-3-oxo-17α-(1,1,2,2,2-pentafluoroethyl)estra-4,15-dien-11β-yl][1,1'-biphenyl]-4-carbonitrile;

11β-(4'-fluoro[1,1'-biphenyl]-4-yl)-17β-hydroxy-17α-(1,1,2,2,2-pentafluoroethyl)estra-4,15-dien-3-one;

17β-hydroxy-17α-(1,1,2,2,2-pentafluoroethyl)-11β-[4-(3-pyridinyl)phenyl]estra-4,15-dien-3-one;

11β-(4-acetylphenyl)-17β-hydroxy-17α-(1,1,2,2,2-pentafluoroethyl)estra-4,9-dien-3-one;

4'-[17β-hydroxy-3-oxo-17α-(1,1,2,2,2-pentafluoroethyl)estra-4,9-dien-11β-yl][1,1'-biphenyl]-4-carbonitrile;

11β-(4'-fluoro[1,1'-biphenyl]-4-yl)-17β-hydroxy-17α-(1,1,2,2,2-pentafluoroethyl)estra-4,9-dien-3-one;

17β-hydroxy-17α-(1,1,2,2,2-pentafluoroethyl)-11β-[4-(3-pyridinyl)phenyl]estra-4,9-dien-3-one;

11β-(4-acetylphenyl)-17β-hydroxy-17α-(1,1,2,2,2-pentafluoroethyl)estra-4,9,15-trien-3-one;

4'-[17β-hydroxy-3-oxo-17α-(1,1,2,2,2-pentafluoroethyl)estra-4,9,15-trien-11β-yl][1,1'-biphenyl]-4-carbonitrile;

11β-(4'-fluoro[1,1'-biphenyl]-4-yl)-17β-hydroxy-17α-(1,1,2,2,2-pentafluoroethyl))estra-4,9,15-trien-3-one;

17β-hydroxy-17α-(1,1,2,2,2-pentafluoroethyl)-11β-[4-(3-pyridinyl)phenyl]estra-4,9,15-trien-3-one;

6'-acetyl-9,11α-dihydro-17β-hydroxy-17α-(1,1,2,2,2-pentafluoroethyl)-4'H-naphth[3',2',1':10,9,11]estr-4-en-3-one;

4-[9,11α-dihydro-17β-hydroxy-3-oxo-17α-(1,1,2,2,2-pentafluoroethyl)-4'H-naphth[3',2',1':10,9,11]estr-4-en-6'-yl]benzonitrile;

9,11α-dihydro-6'-(4-fluorophenyl)-17β-hydroxy-17α-(1,1,2,2,2-pentafluoroethyl)-4'H-naphth[3',2',1':10,9,11]estr-4-en-3-one;

9,11α-dihydro-17β-hydroxy-17α-(1,1,2,2,2-pentafluoroethyl)-6'-(3-pyridinyl)-4'H-naphth[3',2',1':10,9,11]estr-4-en-3-one;

6'-acetyl-9,11α-dihydro-17β-hydroxy-17α-(1,1,2,2,2-pentafluoroethyl)-4'H-naphth[3',2',1':10,9,11]estra-4,15-dien-3-one;

4-[9,11α-dihydro-17β-hydroxy-3-oxo-17α-(1,1,2,2,2-pentafluoroethyl)-4'H-naphth[3',2',1':10,9,11]estra-4,15-dien-6'-yl]benzonitrile;

9,11α-dihydro-6'-(4-fluorophenyl)-17β-hydroxy-17α-(1,1,2,2,2-pentafluoroethyl)-4'H-naphth[3',2',1':10,9,11]estra-4,15-dien-3-one;

9,11α-dihydro-17β-hydroxy-17α-(1,1,2,2,2-pentafluoroethyl)-6'-(3-pyridinyl)-4'H-naphth[3',2',1':10,9,11]estra-4,15-dien-3-one;

17β-hydroxy-11β-(4-hydroxyphenyl)-17α-(1,1,2,2,2-pentafluoroethyl)estra-4,9-dien-3-one;

17β-hydroxy-11β-(4-hydroxyphenyl)-17α-(1,1,2,2,2-pentafluoroethyl)estr-4-en-3-one;

9,11α-dihydro-6',17β-dihydroxy-17α-(1,1,2,2,2-pentafluoroethyl)-4'H-naphth[3',2',1':10,9,11]estr-4-en-3-one;

11β-[4-(acetyloxy)phenyl]-17β-hydroxy-17α-(1,1,2,2,2-pentafluoroethyl)estra-4,9-dien-3-one;

11β-[4-(acetyloxy)phenyl]-17β-hydroxy-17α-(1,1,2,2,2-pentafluoroethyl)estr-4-en-3-one 6'-acetyloxy-9,11α-dihydro-17β-hydroxy-17α-(1,1,2,2,2-pentafluoroethyl)-4'H-naphth[3',2',1':10,9,11]estr-4-en-3-one;

17β-hydroxy-11β-[4-(hydroxymethyl)phenyl]-17α-(1,1,2,2,2-pentafluoroethyl)estra-4,9-dien-3-one;

17β-hydroxy-11β-[4-(hydroxymethyl)phenyl]-17α-(1,1,2,2,2-pentafluoroethyl)estr-4-en-3-one;

9,11α-dihydro-17β-hydroxy-6'-hydroxymethyl-17α-(1,1,2,2,2-pentafluoroethyl)-4'H-naphth[3',2',1':10,9,11]estr-4-en-3-one;

4-[17β-hydroxy-3-oxo-17α-(1,1,2,2,2-pentafluoroethyl)estra-4,9-dien-11β-yl]benzaldehyde;

4-[17β-hydroxy-3-oxo-17α-(1,1,2,2,2-pentafluoroethyl)estr-4-en-11β-yl]benzaldehyde;

9,11α-dihydro-17β-hydroxy-3-oxo-17α-(1,1,2,2,2-pentafluoroethyl)-4'H-naphth[3',2',1':10,9,11]estr-4-en-6'-al;

4-[17β-hydroxy-3-oxo-17α-(1,1,2,2,2-pentafluoroethyl)estra-4,9-dien-11β-yl]benzoic acid methyl ester;

4-[17β-hydroxy-3-oxo-17α-(1,1,2,2,2-pentafluoroethyl)estr-4-en-11β-yl]benzoic acid methyl ester;

9,11α-dihydro-17β-hydroxy-3-oxo-17α-(1,1,2,2,2-pentafluoroethyl)-4'H-naphth[3',2',1':10,9,11]estr-4-en-6'-carboxylic acid methyl ester;

17β-hydroxy-11β-[4-(1-hydroxyethyl)phenyl]-17α-(1,1,2,2,2-pentafluoroethyl)estra-4,9-dien-3-one;

17β-hydroxy-11β-[4-(1-hydroxyethyl)phenyl]-17α-(1,1,2,2,2-pentafluoroethyl)estr-4-en-3-one; or 9,11α-dihydro-17β-hydroxy-6'-(1-hydroxyethyl)-17α-(1,1,2,2,2-pentafluoroethyl)-4'H-naphth[3',2',1':10,9,11]estr-4-en-3-one.

26. 11β-(4-acetylphenyl)-17β-hydroxy-17α-(1,1,2,2,2-pentafluoroethyl)estra-4,9-dien-3-one.

27. A pharmaceutical composition comprising a compound of claim 26 and a pharmaceutically acceptable carrier.

* * * * *